United States Patent [19]

Hausinger

[11] Patent Number: 5,783,436
[45] Date of Patent: Jul. 21, 1998

US005783436A

[54] NUCLEIC ACIDS ENCODING MUTANT UREASE

[75] Inventor: Robert P. Hausinger, East Lansing, Mich.

[73] Assignee: Board of Trustees operating Michigan State University, East Lansing, Mich.

[21] Appl. No.: 967,513

[22] Filed: Nov. 11, 1997

Related U.S. Application Data

[62] Division of Ser. No. 687,645, Jul. 26, 1996.

[51] Int. Cl.[6] .............. C12N 1/21; C12N 15/63; C07H 21/04
[52] U.S. Cl. .............. 435/252.3; 435/320.1; 435/252.33; 536/23.2
[58] Field of Search .............. 536/23.2; 435/227, 435/320.1, 252.3, 252.33

[56] References Cited

U.S. PATENT DOCUMENTS

| | | | |
|---|---|---|---|
| 3,145,086 | 8/1964 | Free et al. | 23/253 |
| 4,066,403 | 1/1978 | Bruschi | 23/230 |
| 4,218,535 | 8/1980 | Ray | 435/12 |
| 5,037,738 | 8/1991 | Lamos et al. | 435/12 |
| 5,093,255 | 3/1992 | Kakimoto et al. | 435/183 |
| 5,137,692 | 8/1992 | Fritz | 422/61 |
| 5,298,399 | 3/1994 | Uozumi et al. | 435/69.1 |

OTHER PUBLICATIONS

Kunkel et al. Proc. Natl. Acad. Sci. 82:488:492 (1985).
Sanger, et al., Proc. Natl. Acad. Sci. USA 74:5463–5467 (1977).
Sambrook et al., Molecular Cloning: A Laboratory Manual. Cold Spring Harbor Laboratory, Cold Spring Harbor, New York (1989) pp. 13.42–13.43.
Mulrooney, S.B. and Hausinger, R.P., Journal of Bacteriology 172:5837–5843 (1990).
Park, I.–S. and Hausinger, R.P., Protein Science 2:1034–1041 (1993).
Mulrooney, et al., J. Gen. Microbiol. 135:1769–1776 (1989).
Todd & Hausinger, J. Biol. Chem. 264:15835–15942 (1989).
Weatherburn, M.W., Anal. Chem. 39:971–974 91967).
Wilkinson, G.N., Biochem. J. 89:324–332 (1961).
Lowry et al., J. Biol. Chem. 193:265–275 (1951).
Park, I.–S. "Mechanistic studies of Klabsiella aerogenes urease and its nickel metallocenter assembly process" Dissertation Abstracts International (1994), vol. 56, No. 3B, p. 1396, 1994.

*Primary Examiner*—Robert A. Wax
*Assistant Examiner*—Kawai Lau
*Attorney, Agent, or Firm*—Ian C. McLeod

[57] ABSTRACT

A mutant urease of *Klebsiella aerogenes* characterized as αH219 having a glutamine (Q) in position 219 in place of histidine (H). The resulting enzyme has a low affinity for substrate (high value of $K_m$) and is particularly useful in assays and test kits for measuring urea concentrations in body fluids.

5 Claims, 7 Drawing Sheets

```
241  CCCGAATCTGGCTGACTTAAGAGAACGTTATGGAACTGACCCCCGAGAAAAGACAAG          300
                      MetGluLeuThrProArgGluLysAspLys

301  CTGTGTGCTGTTACCGCCGCGCTGGTGGCCGGAGCGTCCTGGCCCGGCCCTGAAGCTC          360
     LeuLeuLeuPheThrAlaAlaLeuValAlaGluAlaArgLeuAlaArgGlyLeuLysLeu

361  AACTATCCGGAGTCCGTGGCCCTGGCCCTTTATATGGAAGGCGCTCGGACGGC              420
     AsnTyrProGluSerValAlaLeuIleSerAlaPheIleMetGluGlyAlaArgAspGly

421  AAAAGCGTGGCCTCGCTGATGGAGGAAGGCCGTCACGTCCTGACCCGCGAGCAGGTGATG       480
     LysSerValAlaSerLeuMetGluGluGlyArgHisValLeuThrArgGluGlnValMet

481  GAGGGCGTCCCGGAAATGATCCCGGATATCCAGGTCGAAGCCACCTTCCCGGACGGCTCG       540
     GluGlyValProGluMetIleProAspIleGlnValGluAlaThrPheProAspGlySer

541  AAGCTGGTCACCGTTCACAACCCGATTATCTGAGGTAGCGCCATGATCCCGGTGAATAT        600
     LysLeuValThrValHisAsnProIleIleEnd     MetIleProGlyGluTyr

601  CACGTTAAGCCCGGTCAGATAGCCCTGAATACCGGCAACCTGTCGCGGTCGTT              660
     HisValLysProGlyGlnIleAlaLeuAsnThrGlyArgAlaThrCysArgValValVal

661  GAGAACCACGGCGATCGGCCGATTCAGGTCGGTTCGCCACTACCATTCGCCGAGGTTAAC       720
     GluAsnHisGlyAspArgProIleGlnValGlySerHisTyrHisPheAlaGluValAsn

721  CCGGGCTGAAGTTGACCTGCAGCAGGCCGCCGCTATCGCCTGAATATCCCGGGGGC           780
     ProAlaLeuLysPheAspArgGlnAlaAlaGlyTyrArgLeuAsnIleProAlaGly

781  ACGGCGGTACGCTTTGAACCGGCCAGAAACGCGAGGTCGAGCTGGCCTTCGCCGGT           840
     ThrAlaValArgPheGluProGlyGlnLysArgPheGluLeuValAlaPheAlaGly
```

FIG. IA

```
841  CACCGGCGCCGTCTTCGGCTTCCGCGGCGAGGTCATGGGCCCTCTGGAGGTAAACGATGAG    900
     HisArgAlaValPheGlyPheArgGlyGluValMetGlyProLeuGluValAsnAspGlu
                                                           MetSe

901  TAATATTTCACGCCAGGCCTATGCCGATATGTTCGGCCCCACCGTCGGCGACAAGGTGCG    960
     End
       rAsnIleSerArgGlnAlaTyrAlaAspMetPheGlyProThrValGlyAspLysValAr

961  CCTGGCAGATACCGAGCTGTGGATCGAGGTGGAGGACGATTTGACCACCTACGGGAAGA   1020
     gLeuAlaAspThrGluLeuTrpIleGluValGluAspAspLeuThrThrTyrGlyGluGl

1021 GGTCAAATTCGGCGGCAAAGTGATCCGCGACGGCATGGGCCAGGACAGATGCTGGC      1080
     uValLysPheGlyGlyGlyLysValIleArgAspGlyMetGlyGlnMetLeuAl

1081 CGCCGACTGTGTCGACCTGGTCGTGCTCACCAACGCGTTGATCGTCGATCACTGGGGATCGT 1140
     aAlaAspCysValAspLeuValValLeuThrAsnAlaLeuIleValAspHisTrpGlyIleVa

1141 TAAGGCCGATATCGGCGTGAAGGACGGCCATCTTCGCCATCGGCAAAGCCGGCAACCC    1200
     lLysAlaAspIleGlyValLysAspGlyHisLeuArgIlePheAlaIleGlyLysAlaGlyAsnPr

1201 CGACATCCAGCCCAACGTCACCAACGTCACCATCCCCATCGGCGACGAAGTGATCGCCGCCGA 1260
     oAspIleGlnProAsnValThrIleProIleGlyAlaAlaThrGluValIleAlaAlaGl

1261 AGGAAAAATTGTCACCGCGGGGATCGATACCCATATTCACTGATCTGTCCGCAGCA      1320
     uGlyLysIleValThrAlaGlyIleGlyIleAspThrHisIleHisTrpIleCysProGlnGl
  ^[[K

1321 GGCGGAAGAGGCGCTGGTCTCTGGCGTGACCACCATGGTCGGGGCGGGCACCGGCCCGGC  1380
```

```
                 nAlaGluAlaLeuValSerGlyValThrThrMetValGlyGlyGlyThrGlyProAl
1381 CGCGGGCACCCATGCCACCACCCTGCACCCCGGGCCCGTGTATATCTCACGCATGCTGCA  1440
     aAlaGlyThrHisAlaThrThrCysThrProGlyProTrpTyrIleSerArgMetLeuGl
1441 GGCGGCCGACAGCCTGCCGGTCAATATCGGCCTGCTGGGCAAGGGAAACGTTTCTCAGCC  1500
     nAlaAlaAspSerLeuProValAsnIleGlyLeuLeuGlyLysGlyAsnValSerGlnPr
1501 GGATGCCCTGCGCGAGCAGGTGGGCGCAGGCGTTATTGCCTGAAGATCCAAGAGGACTG  1560
     oAspAlaLeuArgGluGlnValAlaAlaGlyValIleGlyLeuLysIleGlnGluAspTr
1561 GGGCGCCACCCCGGGCGCGGATCGACTGTGCGTTAACCGTCGCCGATGAAATGGACATCCA  1620
     pGlyAlaThrProAlaAlaIleAspCysAlaLeuThrValAlaAspGluMetAspIleGl
1621 GGTCGCCCTGCACAGCGACACCCCTGAATGAATCCGGTTTGTGGAAGACACCCTCGCCGC  1680
     nValAlaLeuHisSerAspThrLeuAsnGluSerGlyPheValGluAspThrLeuAlaAl
1681 CATCGGCGGCACCATCCACACCTTCCATACCGAAGGGGCCGGCGGCCATGGCC  1740
     aIleGlyGlyThrIleHisThrPheHisThrGluGlyAlaGlyGlyHisAlaPr
1741 GGACATCATCACCGCTGCGCCCACCCGAACATTTGCCTGCTCGTCCACCAACCTAAGCT  1800
     oAspIleIleThrAlaCysAlaHisProAsnIleLeuProSerSerThrAsnProThrLe
```

FIG. 1D

```
1801 GCCCTACACCCTCAACACCATCGATGAACATCTCGATATGCTGATGGTCTGCCACCATCT 1860
     uProTyrThrLeuAsnThrIleAspGluHisLeuAspMetLeuMetValCysHisHisLe

1861 GGACCCGGACATCGCCGAGGACGTGCCCTTTGCCGAGTCGCCGCATTCGCCGGGAAACCAT 1920
     uAspProAspIleAlaGluAspValAlaPheAlaGluSerArgIleArgArgGluThrIl

1921 CGCTGCGGAAGACGTGCTGCACGATCTCGGCGCCTTCTCGCTCACCTCCTCCGATTCGCA 1980
     eAlaAlaGluAspValLeuHisAspLeuGlyAlaPheSerLeuThrSerSerAspSerGl

1981 GGCCATGGGCCGTCGGGGAAGTGATTCTCCGCACCTGGCAGGTGGCGCATCGCATGAA 2040
     nAlaMetGlyArgValGlyGluValIleLeuArgThrTrpGlnValAlaHisArgMetLy

2041 GGTGCAGCGCGGAGCGCTGGCGGCGGAGGAGACCGGGGATAACGACACAACTTCCGGTGAAGCG 2100
     sValGlnArgGlyAlaAlaLeuAlaGluAlaGluThrGlyAspAsnAspAsnPheArgValLysAr

2101 CTACATCGCCAAATACACCATCAACCCGGCTGACCTGACGCTGCATCGGCATGCGAACACGAAGTCGG 2160
     gTyrIleAlaLysTyrThrIleAsnProAlaLeuThrHisGlyIleAlaHisGluValGl

2161 ATCCATTGAGGTGGGTAAGCTGGACCTCGTGGTCTGTTGGTCACCAGCCTTCTTCGGCGT 2220
     ySerIleGluValGlyLysLeuAspLeuValValAlaAspLeuValValTrpSerProAlaPhePheGlyVa
```

```
2221  GAAACCGGCCACCGTGATCAAAGGCGGCATGATCGCCGATGGGCCGATATCAA    2280
      lLysProAlaThrValIleLysGlyGlyMetIleAlaIleAlaProMetGlyAspIleAs

2281  TGCCTCTATTCCGACCCCGCAGCCGGTGCACTACCGCCCCGATGTTTGGCGCTGGGCAG    2340
      nAlaSerIleProThrProGlnProValHisTyrArgProMetPheGlyAlaLeuGlySe

2341  CGCCCGCCATCACTGCCGCCTCACCTTCCTGTCGCAGGCGGCAGCCAATGGCTTGC    2400
      rAlaArgHisHisCysArgLeuThrPheLeuSerGlnAlaAlaAlaAlaAsnGlyValAl

2401  CGAGCGGCTGAACCTGGTGCAGCGCGATCGCCGTGGTGAAAGGCTGCCGTACGGTGCAGAA    2460
      aGluArgLeuAsnLeuArgSerAlaIleAlaValValLysGlyCysArgThrValGlnLy

2461  AGCCGACATGGTGCACAACAGTCTGCAGCCTAACATCACCGTCGACGCCCAGACCTATGA    2520
      sAlaAspMetValHisAsnSerLeuGlnProAsnIleThrValAspAlaGlnThrTyrGl

2521  GGTGCGGGTGGATGGCGAACTTATCACCAGCGAGCCGGCAGACGTTCTGCCGATGGCGCA    2580
      uValArgValAspGlyGluLeuIleThrSerGluProAlaAspValLeuProMetAlaGl

2581  ACGATATTTCTGTTTAAGGAGAGCGGATGCTTTATTTAACTCAACGTCTGGAGATCCC    2640
      nArgTyrPheLeuPheEnd
```

FIG. IE

NUCLEIC ACIDS ENCODING MUTANT UREASE

This is a divisional of copending application Ser. No. 08/687,645 filed on Jul. 26, 1996.

BACKGROUND OF THE INVENTION

(1) Summary of the Invention

The present invention relates to the use of a mutant urease to convert urea to carbonic acid and ammonia, particularly in an assay to measure urea concentrations. In particular, the present invention relates to the mutant urease which is characterized as αH219Q.

(2) Description of Related Art

*Klebsiella aerogenes* urease and the DNA encoding it are described by Mulrooney, S. B. and Hausinger, R. P., in Journal of Bacteriology 172:5837–5843 (1990). The urease genes include ureA, ureB and ureC encoding the γ, β and α subunits of the enzyme.

Mutagenesis of various sites in the urease DNA of *Klebsiella aerogenes* is described by Park, I.-S. and Hausinger, R. P., in Protein Science 2:1034–1041 (1993). In particular, position 219 of the α subunit (αH219) was modified from histidine (H) to alanine (A). This change resulted in a diminishment of specific activity and an increase in the value of $K_m$ for the purified enzyme. Thus it was determined that the amino acid at position 219 was important to the binding affinity of urease to the substrate (urea).

The prior art has described numerous methods and test kits for using urease to assay for urea in body fluids, such as urine and blood plasma, and other biological materials. The presence of abnormal levels of urea is indicative of disease. Various calorimetric methods are used to detect a pH change or to otherwise detect the reaction products. Illustrative of the extensive prior art are U.S. Pat. Nos. 3,145,086 to Free et al; 4,066,403 to Bruschi; 4,218,535 to Ray; 5,093,255 to Kakimoto et al; 5,037,738 to Lamos et al; 5,137,692 to Fritz, and 5,298,399 to Uozumi et al. Ureases are thus commercially important, particularly in the medical field, although they do have non-medical uses.

OBJECTS

An object of the present invention is to provide a mutant urease which has improved enzyme kinetic properties (higher $K_m$) compared to the natural enzyme. Further, it is an object of the present invention to provide a method and test kit for use of the mutant urease, particularly in an assay of urea concentrations in body tissues. These and other objects will become increasingly apparent by reference to the following description and the drawing.

IN THE DRAWINGS

FIG. 1 shows the nucleotide sequence encoding urease.

DESCRIPTION OF PREFERRED EMBODIMENTS

Figure 2:
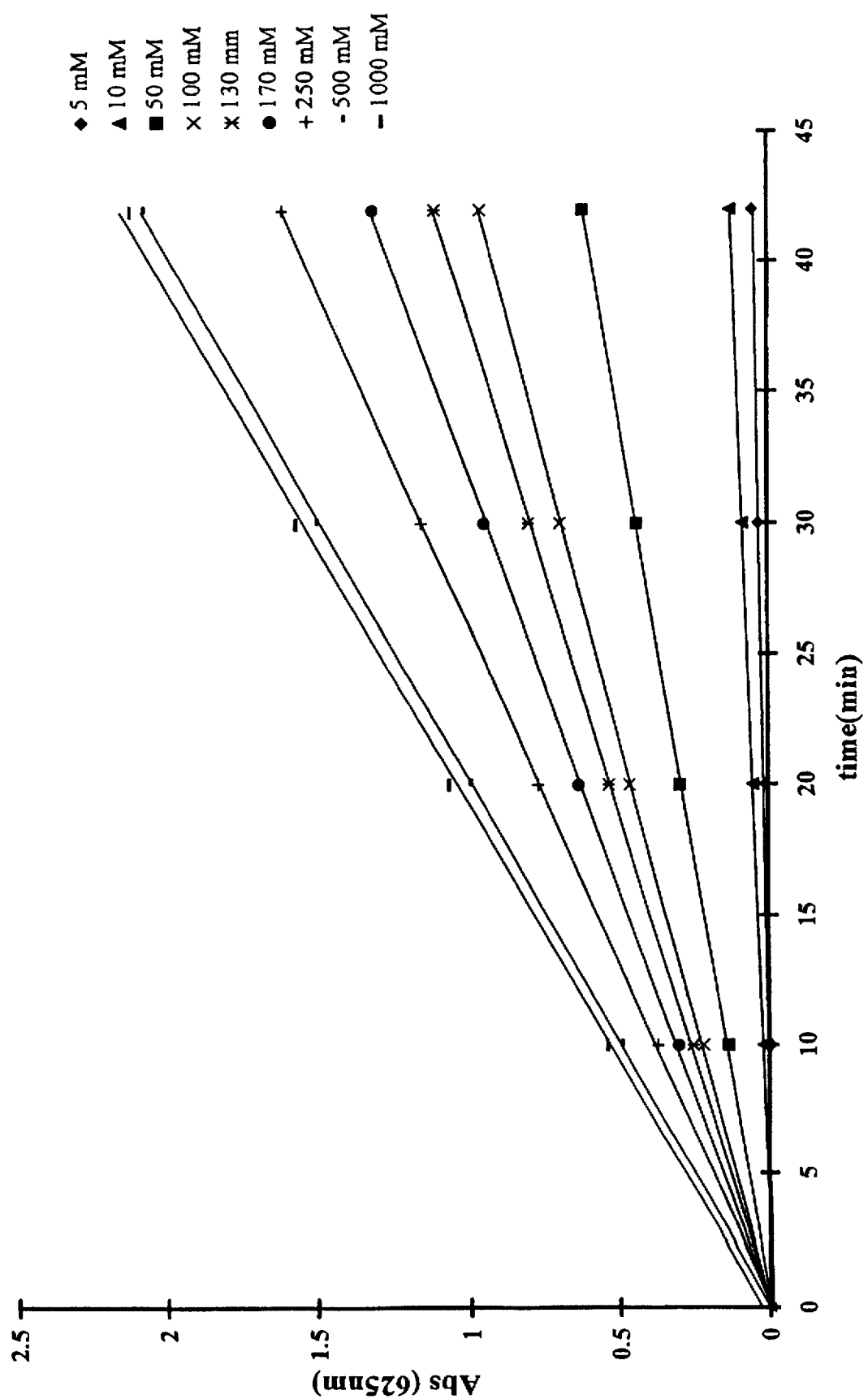
FIG. 2 is a graph showing absorbance arising from conversion of released ammonia into indophenol as a function of time for urease αH219Q incubated at different concentrations of urea.

The present invention relates to a urease of *Klebsiella aerogenes* having a modified urease α subunit, designated as αH219Q, having glutamine as substituent number 219 of the α subunit as set forth in SEQ ID NO:5.

The present invention also relates to a method for converting urea to carbonic acid and ammonia with an enzyme, the improvement which comprises using a urease of *Klebsiella aerogenes* having a modified α subunit, designated as H219Q, having glutamine as substituent 219 of the α subunit for the conversion as set forth in SEQ ID NO:5, wherein the urease has a low affinity for the urea and thus a higher $K_m$ as compared to αH219.

The present invention further relates to a method for assaying for urea in a body fluid by conversion of the urea to carbonic acid and ammonia as products with a urease and detecting the products, the improvement which comprises using a urease of *Klebsiella aerogenes* having a modified a subunit, designated as H219Q, having glutamine as substituent 219 of the α subunit as set forth in SEQ ID NO:5 for the conversion to the products in the assay which are then detected.

The present invention further relates to a test kit for assaying for urea in a body fluid by conversion of urea to carbonic acid and ammonia as products with an enzyme including a means for detecting one or more of the products of the urea, the improvement which comprises: providing in the kit a urease of *Klebsiella aerogenes* having glutamine as substituent 219 of the α subunit as set forth in SEQ ID NO:5 for use to make the conversion.

The segment of urease is referred to as UreA, UreB and UreC. The gene is referred to in the same manner except the first letter is lower case and the gene designation is in italics (ureA, ureB and ureC).

The nucleotide sequence encoding H219Q mutant urease is set forth in SEQ ID NO:1. The UreA peptide is encoded by nucleotides 271–573 in this sequence (SEQ ID NO:3). UreB is encoded by nucleotides 583–903 (SEQ ID NO:4). UreC is encoded by nucleotides 896–2599 (SEQ ID NO:5). This sequence is identical to that in the wild-type organism except for one base pair change at position 1552 of FIG. 1 (within ureC) that was mutated by using the following oligonucleotide primer: GAAGATCCAAGAGGACTGG (SEQ ID NO:2). The DNA is contained in plasmid pKAU17αH219Q in the bacterium in *Escherichia coli* strain DH5. This strain was deposited on Jul. 12, 1996 under the Budapest Treaty with the American Type Culture Collection, Rockville, Md. as ATCC 98103. The strain is available subject to the provisions of the Budapest Treaty and the patent laws.

EXAMPLE 1

Site directed mutagenesis was used to create a mutant capable of forming αH219Q urease, and the protein was partially purified and characterized.

Site-directed mutagenesis

For generation of αH219Q, a 1.4-kb SacI-SmaI fragment of pKAU17 (Mulrooney et al., J. Gen. Microbiol. 135:1769–1776 (1989)) was subcloned into M13 mp18 and mutagenized by the method of Kunkel et al (Proc. Natl. Acad. Sci. 82:488–492 (1985)). A 1.1-kb BamH1-SalI fragment of plasmid was used. Uracil-containing single-stranded template DNA was prepared from *E. coli* CJ236 (dut1 ung1 thi-1 relA1/pCJ105[cam$^r$F']). Mutagenized phage were isolated in *E. coli* MV1193 (Δ[lacI-proAB] rpsL thi endA spcB15 hsdR4 Δ[srl-recA]306::Tn10[tet$^r$] F'[traD36 proAB+lacI$^q$ lacZΔM15). The oligonucleotide was synthesized by using an Applied Biosystems Model 394 DNA synthesizer at the Michigan State University Macromolecular Structural Facility, East Lansing, Mich. GAAGATC-CAAGAGGACTGG (SEQ ID NO:2). This primer was used to alter the conserved histidine codon αH219 to encode glutamine. Site-directed mutants were identified by DNA sequencing and subcloned back into pKAU17 on a 0.8-kb MluI-BamI fragment. These regions were completely sequenced by using Sequenase 2.0 (United States Biochemicals) and the single-strand DNA sequencing method of Sanger et al, Proc. Natl. Acad. Sci. USA 74:5463–5467 (1977) to ensure that no other mutations had been introduced into M13. After subcloning, the mutated sequences were again confirmed by double-strand DNA sequencing methods (Sambrook et al., Molecular Cloning: A Laboratory Manual. Cold Spring Harbor Laboratory, Cold Spring Harbor, N.Y. (1989)).

Enzyme Purification The urease was partially purified from *E. coli* DH5 carrying the site-directed mutant of pKAU17 by procedures described previously (Todd & Hausinger, J. Biol. Chem. 264:15835–15942 (1989)), except that cells were grown in LB medium containing 1 mM $NiCl_2$.

Assay of enzyme activity

Figure 3:
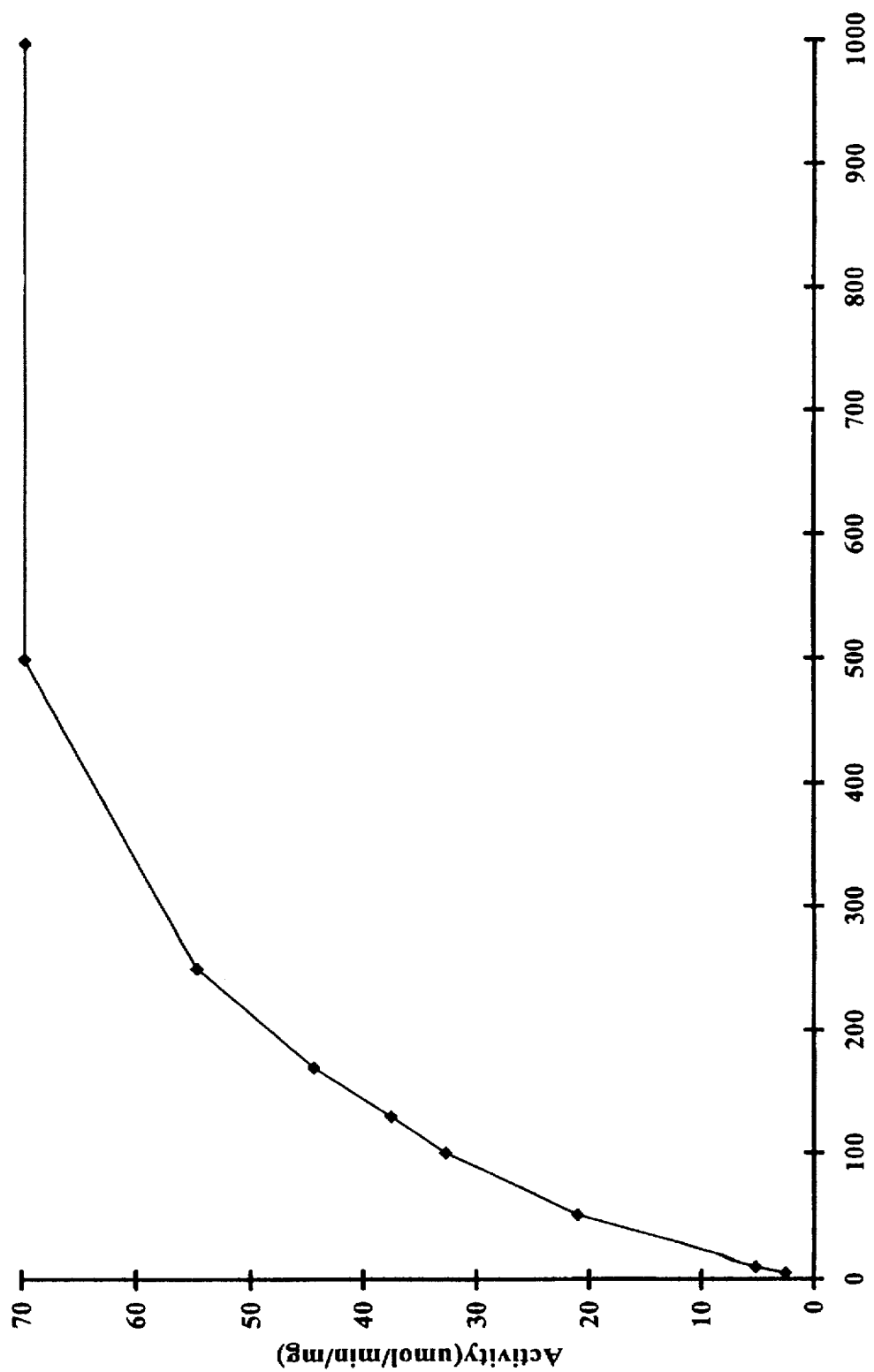
FIG. 3 is a graph showing activity of urease αH21Q versus concentration of urea in mM.

Urease activity for αH219Q enzyme was assayed in 25 mM MES, pH 6.2, or 25 mM HEPES, pH 7.75, 0.5 mM EDTA, and 1M urea (the urea concentration was varied for kinetics measurements). One unit of enzyme activity is defined as the amount of enzyme required to degrade 1 μmol of urea per minute at 37° C. FIG. 2 shows the results at various concentrations of urea. Linear regression analysis of the released ammonia, determined by conversion to indophenol (Weatherburn, M. W., Anal. Chem. 39:971–974 (1967)), versus time yielded the initial rates. A plot of initial rates as a function of urea concentration is shown in FIG. 3. For comparison, analogous studies with the wild type enzyme (Todd and Hausinger, J. Biol. Chem. 264:15835–15942 (1989)) show that maximal rates are achieved by approximately 15 mM urea concentration. Calculation of kinetic constants made use of the method of Wilkinson, G. N., Biochem. J. 80:324–332 (1961). Protein was assayed by the method of Lowry et al, J. Biol. Chem. 193:265–275 (1951)).

Urease H219Q has a $K_m$ value of approximately 175 mM or about 75-fold that of the native enzyme. The rate of H219Q enzyme at its pH optimum (pH 6.2) is about 45% of that measured for the wild-type urease at its pH optimum at pH 7.75.

EXAMPLE 2

Feasibility studies to demonstrate the usefulness of H219Q urease in a test kit for analysis of urea levels in body fluids.

Approximately 0.75 mg aliquots of H219Q urease were diluted with 5 ml of either 10 mM citric acid, 10 mM MES, 10 mM HEPES, or 10 mM phosphate buffers (pH 6.2 in all cases), each containing the pH indicator phenol red at a concentration of 0.04%. The solutions were used to wet cellulose strips which were then allowed to air dry, resulting in yellow-colored test strips. Samples (5 μl) containing urea at concentrations of 0.01, 0.02, 0.05, 0.10, 0.20, 0.33, 0.50, and 1.0M were added to each of the test strips. The times (in seconds) required to detect pink coloration at the sites of addition were measured. Sample data is tabulated below:

TABLE 1

H219Q Urease Test Kit Feasibility Study

| Concentration of Urea (M) | Time required (sec) for formation of pink color in the following buffers | | | |
|---|---|---|---|---|
| | Citrate | MES | HEPES | Phosphate |
| 0.01 | 110 | 200 | 120 | 240 |
| 0.02 | 42 | 87 | 56 | 68 |
| 0.05 | 26 | 40 | 27 | 40 |
| 0.10 | 20 | 28 | 18 | 27 |
| 0.20 | 9 | 12 | 9 | 14 |
| 0.33 | 6 | 9 | 6 | 10 |
| 0.50 | 4 | 6 | 4 | 6 |
| 1.0 | 3 | 5 | 3 | 5 |

Various pH indicators, such as bromothymol blue or bromocresol purple can be used. There is little dependence on the buffer used in the assay, but citrate or HEPES buffers appear to allow the most rapid development of color, whereas, color development is slower in MES or phosphate buffers. The time required for color development can be adjusted by altering the amount of enzyme impregnated into the test strip. In addition, the endpoint can be varied by monitoring the time required for the test strip color intensities to reach that of a colored gage that could be included in a kit. These results demonstrate that test strips containing H219Q enzyme can be used for simple, rapid, and reliable measurements of urea concentrations over a concentration range that is clinically useful.

This procedure is readily adaptable to use in a test kit with a variety of formats including a test strip or sheet made of a wide variety of materials well known to those skilled in the art. The kit could also include ingredients in separate containers which are combined for a testing as is also well known. Preferably the ingredients are in a dry form and water is added in a solution with the urea. Body fluid samples can be added directly to the dry urease, any buffers and the indicator. Various indicators are well known to those skilled in the art which react with the products produced (ammonium carbonate) or the urea, or a change in condition of the reaction solution (such as pH).

---

I claim:

1. A DNA as set forth in SEQ ID NO:1.

2. A DNA as carried on plasmid pKAU17 αH219Q in *Escherichia coli* strain DH5 deposited as ATCC 98103 which produces a mutant urease designated as αH219Q.

3. A plasmid designated as pKAU17 αH219Q carried in *Escherichia coli* strain DH5 deposited as ATCC 98103 which contains a DNA encoding a mutant urease designated as αH219Q.

4. A bacterium containing a DNA as carried in plasmid pKAU17 αH219Q in *Escherichia coli* strain DH5 deposited as ATCC 98103 which produces a mutant urease designated as αH219Q.

5. The bacterium of claim 4 which is *Escherichia coli* strain DH5.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 2400
( B ) TYPE: nucleotides ( C ) STRANDEDNESS: Single
( D ) TOPOLOGY: Linear ( i i ) MOLECULE TYPE:
    ( A ) DESCRIPTION: cDNA ( i i i ) HYPOTHETICAL: No ( i v ) ANTI-SENSE: No ( v i ) ORIGINAL SOURCE:
    ( A ) ORGANISM: Klebsiella aerogenes
    ( B ) STRAIN: CG253
    ( C ) INDIVIDUAL ISOLATE:
    ( G ) CELL TYPE: N/A ( i x ) FEATURE:
    ( A ) NAME/KEY: cDNA encoding mutant urease αH219Q
    ( B ) LOCATION: Modification at position 1312 to glutamine
    ( C ) IDENTIFICATION METHOD: Sequencing
    ( D ) OTHER INFORMATION:

( x i ) SEQUENCE DESCRIPTION: SEQ ID NO:1:

| | | | | | |
|---|---|---|---|---|---|
| CCCCGAATCT | GGCTGACTTA | AGAGAACGTT | ATGGAACTGA | CCCCCCGAGA | 50 |
| AAAAGACAAG | CTGTTGCTGT | TTACCGCCGC | GCTGGTGGCG | GAGCGTCGCC | 100 |
| TGGCCCGCGG | CCTGAAGCTC | AACTATCCGG | AGTCCGTGGC | CCTGATCAGC | 150 |
| GCCTTTATTA | TGGAAGGCGC | TCGGGACGGC | AAAAGCGTGG | CCTCGCTGAT | 200 |
| GGAGGAAGGC | CGTCACGTCC | TGACCCGCGA | GCAGGTGATG | GAGGGCGTCC | 250 |
| CGGAAATGAT | CCCGGATATC | CAGGTCGAAG | CCACCTTCCC | GGACGGCTCG | 300 |
| AAGCTGGTCA | CCGTTCACAA | CCCGATTATC | TGAGGTAGCG | CCATGATCCC | 350 |
| CGGTGAATAT | CACGTTAAGC | CCGGTCAGAT | AGCCCTGAAT | ACCGGCCGGG | 400 |
| CAACCTGTCG | CGTGGTCGTT | GAGAACCACG | GCGATCGGCC | GATTCAGGTC | 450 |
| GGTTCGCACT | ACCATTTCGC | CGAGGTTAAC | CCGGCGCTGA | AGTTCGACCG | 500 |
| TCAGCAGGCC | GCCGGCTATC | GCCTGAATAT | CCCGGCGGGC | ACGGCGGTAC | 550 |
| GCTTTGAACC | CGGCCAGAAA | CGCGAGGTCG | AGCTGGTGGC | CTTCGCCGGT | 600 |
| CACCGCGCCG | TCTTCGGCTT | CCGCGGCGAG | GTCATGGGCC | CTCTGGAGGT | 650 |
| AAACGATGAG | TAATATTTCA | CGCCAGGCCT | ATGCCGATAT | GTTCGGCCCC | 700 |
| ACCGTCGGCG | ACAAGGTGCG | CCTGGCAGAT | ACCGAGCTGT | GGATCGAGGT | 750 |
| GGAGGACGAT | TTGACCACCT | ACGGGGAAGA | GGTCAAATTC | GGCGGCGGCA | 800 |
| AAGTGATCCG | CGACGGCATG | GGCCAGGGAC | AGATGCTGGC | CGCCGACTGT | 850 |
| GTCGACCTGG | TGCTCACCAA | CGCGTTGATC | GTCGATCACT | GGGGGATCGT | 900 |
| TAAGGCCGAT | ATCGGCGTGA | AGGACGGCCG | GATCTTCGCC | ATCGGCAAAG | 950 |
| CCGGCAACCC | CGACATCCAG | CCCAACGTCA | CCATCCCCAT | CGGCGCTGCG | 1000 |
| ACGGAAGTGA | TCGCCGCCGA | AGGAAAAATT | GTCACCGCCG | GCGGGATCGA | 1050 |
| TACCCATATT | CACTGGATCT | GTCCGCAGCA | GGCGGAAGAG | GCGCTGGTCT | 1100 |
| CTGGCGTGAC | CACCATGGTC | GGCGGCGGCA | CCGGCCCGGC | CGCGGGCACC | 1150 |
| CATGCCACCA | CCTGCACCCC | GGGCCCGTGG | TATATCTCAC | GCATGCTGCA | 1200 |
| GGCGGCCGAC | AGCCTGCCGG | TCAATATCGG | CCTGCTGGGC | AAGGGAAACG | 1250 |
| TTTCTCAGCC | GGATGCCCTG | CGCGAGCAGG | TGGCGGCAGG | CGTTATTGGC | 1300 |
| CTGAAGATCC | AAGAGGACTG | GGGCGCCACC | CCGGCGGCGA | TCGACTGTGC | 1350 |

-continued

| | | | | | |
|---|---|---|---|---|---|
| GTTAACCGTC | GCCGATGAAA | TGGACATCCA | GGTCGCCCTG | CACAGCGACA | 1400 |
| CCCTGAATGA | ATCCGGTTTT | GTGGAAGACA | CCCTCGCCGC | CATCGGCGGG | 1450 |
| CGCACCATCC | ACACCTTCCA | TACCGAAGGG | GCCGGCGGCG | GCCATGCGCC | 1500 |
| GGACATCATC | ACCGCCTGCG | CCCACCCGAA | CATTTGCCG | TCGTCCACCA | 1550 |
| ACCCAACGCT | GCCCTACACC | CTCAACACCA | TCGATGAACA | TCTCGATATG | 1600 |
| CTGATGGTCT | GCCACCATCT | GGACCCGGAC | ATCGCCGAGG | ACGTGGCCTT | 1650 |
| TGCCGAGTCG | CGCATTCGCC | GGGAAACCAT | CGCTGCGGAA | GACGTGCTGC | 1700 |
| ACGATCTCGG | CGCCTTCTCG | CTCACCTCCT | CCGATTCGCA | GGCCATGGGC | 1750 |
| CGCGTCGGGG | AAGTGATTCT | CCGCACCTGG | CAGGTGGCGC | ATCGCATGAA | 1800 |
| GGTGCAGCGC | GGAGCGCTGG | CGGAGGAGAC | CGGGGATAAC | GACAACTTCC | 1850 |
| GCGTGAAGCG | CTACATCGCC | AAATACACCA | TCAACCCGGC | GCTGACCCAC | 1900 |
| GGCATCGCAC | ACGAAGTCGG | ATCCATTGAG | GTGGGTAAGC | TGGCTGACCT | 1950 |
| CGTGGTCTGG | TCACCAGCCT | TCTTCGGCGT | GAAACCGGCC | ACCGTGATCA | 2000 |
| AAGGCGGCAT | GATCGCCATC | GCGCCGATGG | GCGATATCAA | TGCCTCTATT | 2050 |
| CCGACCCCGC | AGCCGGTGCA | CTACCGCCCG | ATGTTTGGCG | CGCTGGGCAG | 2100 |
| CGCCCGCCAT | CACTGCCGCC | TCACCTTCCT | GTCGCAGGCG | GCGGCAGCCA | 2150 |
| ATGGCGTTGC | CGAGCGGCTG | AACCTGCGCA | GCGCGATCGC | CGTGGTGAAA | 2200 |
| GGCTGCCGTA | CGGTGCAGAA | AGCCGACATG | GTGCACAACA | GTCTGCAGCC | 2250 |
| TAACATCACC | GTCGACGCCC | AGACCTATGA | GGTGCGGGTG | GATGGCGAAC | 2300 |
| TTATCACCAG | CGAGCCGGCA | GACGTTCTGC | CGATGGCGCA | ACGATATTTT | 2350 |
| CTGTTTTAAG | GAGAGCGGAT | GCTTTATTTA | ACTCAACGTC | TGGAGATCCC | 2400 |

( 2 ) INFORMATION FOR SEQ ID NO:2:

( i ) SEQUENCE CHARACTERISTICS:
        ( A ) LENGTH: 19
        ( B ) TYPE: nucleotides
        ( C ) STRANDEDNESS: Single
        ( D ) TOPOLOGY: Linear ( i i ) MOLECULE TYPE:
        ( A ) DESCRIPTION: oligonucleotide ( i i i ) HYPOTHETICAL: No ( i v ) ANTI-SENSE: No ( v i ) ORIGINAL SOURCE:
        ( A ) ORGANISM: N/A
        ( B ) STRAIN: N/A
        ( C ) INDIVIDUAL ISOLATE: N/A
        ( G ) CELL TYPE: N/A ( i x ) FEATURE:
        ( A ) NAME/KEY: glutaminyl mutating
        ( B ) LOCATION: nucleotide
        ( C ) IDENTIFICATION METHOD: Sequencing
        ( D ) OTHER INFORMATION: Synthetic
                oligonucleotide ( x i ) SEQUENCE DESCRIPTION: SEQ ID NO:2:

GAAGATCCAA GAGGACTGG                                                            19

( 2 ) INFORMATION FOR SEQ ID NO:3:

( i ) SEQUENCE CHARACTERISTICS:
        ( A ) LENGTH: 100

( B ) TYPE: amino acids
                    ( C ) STRANDEDNESS: Single
                    ( D ) TOPOLOGY: Linear ( i i ) MOLECULE TYPE:
                    ( A ) DESCRIPTION: Protein ( i i i ) HYPOTHETICAL: No ( i v ) ANTI-SENSE: No ( v i ) ORIGINAL SOURCE:
                    ( A ) ORGANISM: N/A
                    ( B ) STRAIN: N/A
                    ( C ) INDIVIDUAL ISOLATE: N/A
                    ( G ) CELL TYPE: N/A ( i x ) FEATURE:
                    ( A ) NAME/KEY: subunit UreA
                    ( B ) LOCATION:
                    ( C ) IDENTIFICATION METHOD: Sequencing
                    ( D ) OTHER INFORMATION: encoded subunit of
                            mutant urease ( x i ) SEQUENCE DESCRIPTION: SEQ ID NO:3:

```
                                Met Glu Leu Thr Pro
                                                  5

Arg Glu Lys Asp Lys Leu Leu Leu Phe Thr Ala
                10                      15

Ala Leu Val Ala Glu Arg Arg Leu Ala Arg Gly
            20                  25

Leu Lys Leu Asn Tyr Pro Glu Ser Val Ala Leu
            30              35

Ile Ser Ala Phe Ile Met Glu Gly Ala Arg Asp
    40                      45

Gly Lys Ser Val Ala Ser Leu Met Glu Glu Gly
50                      55                      60

Arg His Val Leu Thr Arg Glu Gln Val Met Glu
                65                      70

Gly Val Pro Glu Met Ile Pro Asp Ile Gln Val
                75                  80

Glu Ala Thr Phe Pro Asp Gly Ser Lys Leu Val
            85                  90

Thr Val His Asn Pro Ile Ile
         95              100
```

( 2 ) INFORMATION FOR SEQ ID NO:4:

( i ) SEQUENCE CHARACTERISTICS:
                    ( A ) LENGTH: 106
                    ( B ) TYPE: amino acids
                    ( C ) STRANDEDNESS: Single
                    ( D ) TOPOLOGY: Linear ( i i ) MOLECULE TYPE:
                    ( A ) DESCRIPTION: protein ( i i i ) HYPOTHETICAL: No ( i v ) ANTI-SENSE: No ( v i ) ORIGINAL SOURCE:
                    ( A ) ORGANISM: N/A
                    ( B ) STRAIN: N/A
                    ( C ) INDIVIDUAL ISOLATE: N/A
                    ( G ) CELL TYPE: N/A ( i x ) FEATURE:
                    ( A ) NAME/KEY: subunit UreB (B) LOCATION:
(C) IDENTIFICATION METHOD: Sequencing
(D) OTHER INFORMATION: encoded subunit (xi) SEQUENCE DESCRIPTION: SEQ ID NO:4:

```
                                        Met   Ile   Pro   Gly   Glu   Tyr
                                                                        5

His   Val   Lys   Pro   Gly   Gln   Ile   Ala   Leu   Asn   Thr   Gly   Arg
                  10                            15

Ala   Thr   Cys   Arg   Val   Val   Val   Glu   Asn   His   Gly   Asp   Arg
20                            25                            30

Pro   Ile   Gln   Val   Gly   Ser   His   Tyr   His   Phe   Ala   Glu   Val
                  35                      40                                45

Asn   Pro   Ala   Leu   Lys   Phe   Asp   Arg   Gln   Gln   Ala   Ala   Gly
                        50                            55

Tyr   Arg   Leu   Asn   Ile   Pro   Ala   Gly   Thr   Ala   Val   Arg   Phe
      60                            65                            70

Glu   Pro   Gly   Gln   Lys   Arg   Glu   Val   Glu   Leu   Val   Ala   Phe
                  75                            80

Ala   Gly   His   Arg   Ala   Val   Phe   Gly   Phe   Arg   Gly   Glu   Val
85                            90                            95

Met   Gly   Pro   Leu   Glu   Val   Asn   Asp   Glu
                  100                     105
```

(2) INFORMATION FOR SEQ ID NO:5:

(i) SEQUENCE CHARACTERISTICS:
        (A) LENGTH: 567
        (B) TYPE: amino acids
        (C) STRANDEDNESS: Single
        (D) TOPOLOGY: Linear (ii) MOLECULE TYPE:
        (A) DESCRIPTION: protein (iii) HYPOTHETICAL: No (iv) ANTI-SENSE: No (vi) ORIGINAL SOURCE:
        (A) ORGANISM: N/A
        (B) STRAIN: N/A
        (C) INDIVIDUAL ISOLATE: N/A
        (G) CELL TYPE: N/A (ix) FEATURE:
        (A) NAME/KEY: subunit UreC
        (B) LOCATION:
        (C) IDENTIFICATION METHOD: Sequencing
        (D) OTHER INFORMATION: Encoded subunit of mutant
            urease (xi) SEQUENCE DESCRIPTION: SEQ ID NO:5:

```
                                        Met   Ser   Asn   Ile   Ser
                                                                  5

Arg   Gln   Ala   Tyr   Ala   Asp   Met   Phe   Gly   Pro   Thr   Val   Gly
                  10                            15

Asp   Lys   Val   Arg   Leu   Ala   Asp   Thr   Glu   Leu   Trp   Ile   Glu
      20                      25                            30

Val   Glu   Asp   Asp   Leu   Thr   Thr   Tyr   Gly   Glu   Glu   Val   Lys
                  35                      40

Phe   Gly   Gly   Gly   Lys   Val   Ile   Arg   Asp   Gly   Met   Gly   Gln
45                            50                      55

Gly   Gln   Met   Leu   Ala   Ala   Asp   Cys   Val   Asp   Leu   Val   Leu
```

-continued

|  |  |  | 60 |  |  | 65 |  |  |  | 70 |
|---|---|---|---|---|---|---|---|---|---|---|
| Thr | Asn | Ala | Leu | Ile | Val | Asp | His | Trp | Gly | Ile | Val | Lys |
|  |  |  | 75 |  |  |  | 80 |  |  |  |
| Ala | Asp | Ile | Gly | Val | Lys | Asp | Gly | Arg | Ile | Phe | Ala | Ile |
|  |  | 85 |  |  |  | 90 |  |  |  | 95 |
| Gly | Lys | Ala | Gly | Asn | Pro | Asp | Ile | Gln | Pro | Asn | Val | Thr |
|  |  |  | 100 |  |  |  | 105 |  |  |
| Ile | Pro | Ile | Gly | Ala | Ala | Thr | Glu | Val | Ile | Ala | Ala | Glu |
| 110 |  |  |  |  | 115 |  |  |  |  | 120 |
| Gly | Lys | Ile | Val | Thr | Ala | Gly | Gly | Ile | Asp | Thr | His | Ile |
|  |  |  | 125 |  |  |  | 130 |  |  |  |  | 135 |
| His | Trp | Ile | Cys | Pro | Gln | Gln | Ala | Glu | Glu | Ala | Leu | Val |
|  |  |  |  | 140 |  |  |  |  | 145 |
| Ser | Gly | Val | Thr | Thr | Met | Val | Gly | Gly | Thr | Gly | Pro |
|  | 150 |  |  |  |  | 155 |  |  |  | 160 |
| Ala | Ala | Gly | Thr | His | Ala | Thr | Thr | Cys | Thr | Pro | Gly | Pro |
|  |  |  | 165 |  |  |  |  | 170 |
| Trp | Tyr | Ile | Ser | Arg | Met | Leu | Gln | Ala | Ala | Asp | Ser | Leu |
| 175 |  |  |  |  | 180 |  |  |  | 185 |
| Pro | Val | Asn | Ile | Gly | Leu | Leu | Gly | Lys | Gly | Asn | Val | Ser |
|  |  | 190 |  |  |  |  | 195 |  |  |  |  | 200 |
| Gln | Pro | Asp | Ala | Leu | Arg | Glu | Gln | Val | Ala | Ala | Gly | Val |
|  |  |  |  | 205 |  |  |  |  | 210 |
| Ile | Gly | Leu | Lys | Ile | Gln | Glu | Asp | Trp | Gly | Ala | Thr | Pro |
|  | 215 |  |  |  |  | 220 |  |  |  |  | 225 |
| Ala | Ala | Ile | Asp | Cys | Ala | Leu | Thr | Val | Ala | Asp | Glu | Met |
|  |  |  | 230 |  |  |  |  | 235 |
| Asp | Ile | Gln | Val | Ala | Leu | His | Ser | Asp | Thr | Leu | Asn | Glu |
| 240 |  |  |  |  | 245 |  |  |  |  | 250 |
| Ser | Gly | Phe | Val | Glu | Asp | Thr | Leu | Ala | Ala | Ile | Gly | Gly |
|  |  | 255 |  |  |  |  | 260 |  |  |  |  | 265 |
| Arg | Thr | Ile | His | Thr | Phe | His | Thr | Glu | Gly | Ala | Gly | Gly |
|  |  |  |  | 270 |  |  |  |  | 275 |
| Gly | His | Ala | Pro | Asp | Ile | Ile | Thr | Ala | Cys | Ala | His | Pro |
|  | 280 |  |  |  |  | 285 |  |  |  |  | 290 |
| Asn | Ile | Leu | Pro | Ser | Ser | Thr | Asn | Pro | Thr | Leu | Pro | Tyr |
|  |  |  | 295 |  |  |  |  | 300 |
| Thr | Leu | Asn | Thr | Ile | Asp | Glu | His | Leu | Asp | Met | Leu | Met |
| 305 |  |  |  |  | 310 |  |  |  |  | 315 |
| Val | Cys | His | His | Leu | Asp | Pro | Asp | Ile | Ala | Glu | Asp | Val |
|  |  |  | 320 |  |  |  |  | 325 |  |  |  |  | 330 |
| Ala | Phe | Ala | Glu | Ser | Arg | Ile | Arg | Arg | Glu | Thr | Ile | Ala |
|  |  |  |  | 335 |  |  |  |  | 340 |
| Ala | Glu | Asp | Val | Leu | His | Asp | Leu | Gly | Ala | Phe | Ser | Leu |
|  | 345 |  |  |  |  | 350 |  |  |  |  | 355 |
| Thr | Ser | Ser | Asp | Ser | Gln | Ala | Met | Gly | Arg | Val | Gly | Glu |
|  |  |  | 360 |  |  |  |  | 365 |
| Val | Ile | Leu | Arg | Thr | Trp | Gln | Val | Ala | His | Arg | Met | Lys |
| 370 |  |  |  |  | 375 |  |  |  |  | 380 |
| Val | Gln | Arg | Gly | Ala | Leu | Ala | Glu | Glu | Thr | Gly | Asp | Asn |
|  |  | 385 |  |  |  |  | 390 |  |  |  |  | 395 |
| Asp | Asn | Phe | Arg | Val | Lys | Arg | Tyr | Ile | Ala | Lys | Tyr | Thr |
|  |  |  |  | 400 |  |  |  |  | 405 |

-continued

| | | | | | | | | | | | |
|---|---|---|---|---|---|---|---|---|---|---|---|
| Ile | Asn 410 | Pro | Ala | Leu | Thr | His 415 | Gly | Ile | Ala | His | Glu 420 | Val |
| Gly | Ser | Ile | Glu 425 | Val | Gly | Lys | Leu | Ala 430 | Asp | Leu | Val | Val |
| Trp 435 | Ser | Pro | Ala | Phe | Phe 440 | Gly | Val | Lys | Pro | Ala 445 | Thr | Val |
| Ile | Lys | Gly 450 | Gly | Met | Ile | Ala | Ile 455 | Ala | Pro | Met | Gly | Asp 460 |
| Ile | Asn | Ala | Ser | Ile 465 | Pro | Thr | Pro | Gln | Pro 470 | Val | His | Tyr |
| Arg | Pro 475 | Met | Phe | Gly | Ala | Leu 480 | Gly | Ser | Ala | Arg | His 485 | His |
| Cys | Arg | Leu | Thr 490 | Phe | Leu | Ser | Gln | Ala 495 | Ala | Ala | Ala | Asn |
| Gly 500 | Val | Ala | Glu | Arg | Leu 505 | Asn | Leu | Arg | Ser | Ala 510 | Ile | Ala |
| Val | Val | Lys 515 | Gly | Cys | Arg | Thr | Val 520 | Gln | Lys | Ala | Asp | Met 525 |
| Val | His | Asn | Ser | Leu 530 | Gln | Pro | Asn | Ile | Thr 535 | Val | Asp | Ala |
| Gln | Thr 540 | Tyr | Glu | Val | Arg | Val 545 | Asp | Gly | Glu | Leu | Ile 550 | Thr |
| Ser | Glu | Pro | Ala 555 | Asp | Val | Leu | Pro | Met 560 | Ala | Gln | Arg | Tyr |
| Phe 565 | Leu | Phe | | | | | | | | | | |